US006467486B1

(12) United States Patent
Kleinschmidt

(10) Patent No.: US 6,467,486 B1
(45) Date of Patent: Oct. 22, 2002

(54) EXTRICATING DEVICE FOR PERSONS WITH SPINAL INJURIES

(76) Inventor: Michael Kleinschmidt, 707 Divot St., Merrill, WI (US) 54452

( * ) Notice: Subject to any disclaimer, the term of this patent is extended or adjusted under 35 U.S.C. 154(b) by 0 days.

(21) Appl. No.: 09/659,723

(22) Filed: Sep. 8, 2000

(51) Int. Cl.[7] .............................................. A61B 19/00
(52) U.S. Cl. ........................... 128/869; 128/870; 5/630
(58) Field of Search ................................. 128/869, 870, 128/874, 876; 5/630, 636, 638, 640

(56) References Cited

U.S. PATENT DOCUMENTS

| | | | | |
|---|---|---|---|---|
| 3,707,734 A | * | 1/1973 | Matthews | 5/81 |
| 3,737,923 A | * | 6/1973 | Prolo | 5/81 |
| 4,211,218 A | * | 7/1980 | Kendrick | 128/870 |
| 4,665,908 A | * | 5/1987 | Calkin | 128/870 |
| 5,027,833 A | * | 7/1991 | Calkin | 128/870 |
| 5,819,747 A | * | 10/1998 | Timms | 128/874 |
| 6,223,749 B1 | * | 5/2001 | Beaty | 128/820 |

* cited by examiner

Primary Examiner—Michael A. Brown
(74) Attorney, Agent, or Firm—Goldstein & Lavas, P.C.

(57) ABSTRACT

An extricating device for persons with spinal injuries including a support board positionable on the back, neck, and head of the person. The support board is conformable to the back, neck, and back of the person. The support board includes a main section and an upper section extending upwardly from the main section. The upper section is positionable under the neck and head of the person. A plurality of straps are coupled with the support board for securing the support board to the person. Each of the straps are adjustable.

2 Claims, 3 Drawing Sheets

EXTRICATING DEVICE FOR PERSONS WITH SPINAL INJURIES

BACKGROUND OF THE INVENTION

The present invention relates to an extricating device for persons with spinal injuries and more particularly pertains to allowing a person having a spinal injury to be moved from a seated position to a horizontal position and onto an awaiting long board.

The use of immobilization devices is known in the prior art. More specifically, immobilization devices heretofore devised and utilized for the purpose of immobilizing a person's-head and neck during transport are known to consist basically of familiar, expected and obvious structural configurations, notwithstanding go the myriad of designs encompassed by the crowded prior art which have been developed for the fulfillment of countless objectives and requirements.

By way of example, U.S. Pat. No. 5,785,058 to Reynolds discloses a device for the immobilization of a patient's head and neck during transport, comprised of a disposable spine board and a series of securing straps. U.S. Pat. No. 4,299,211 to Doynow discloses an extraction splint capable of immobilizing the head, neck and spine of an injured person during transport to a medical facility. U.S. Pat. No. 5,819,747 to Timms discloses an immobilizing vest for extrication of accident victims with a spinal injury.

While these devices fulfill their respective, particular objective and requirements, the aforementioned patents do not describe an extricating device for persons with spinal injuries for allowing a person having a spinal injury to be moved from a seated position to a horizontal position and onto an awaiting long board.

In this respect, the extricating device for persons with spinal injuries according to the present invention substantially departs from the conventional concepts and designs of the prior art, and in doing so provides an apparatus primarily developed for the purpose of allowing a person having a spinal injury to be moved from a seated position to a horizontal position and onto an awaiting long board.

Therefore, it can be appreciated that there exists a continuing need for a new and improved extricating device for persons with spinal injuries which can be used for allowing a person having a spinal injury to be moved from a seated position to a horizontal position and onto an awaiting long board. In this regard, the present invention substantially fulfills this need.

SUMMARY OF THE INVENTION

In the view of the foregoing disadvantages inherent in the known types of immobilization devices now present in the prior art, the present invention provides an improved extricating device for persons with spinal injuries. As such, the general purpose of the present invention, which will be described subsequently in greater detail, is to provide a new and improved extricating device for persons with spinal injuries which has all the advantages of the prior art and none of the disadvantages.

To attain this, the present invention essentially comprises a support board positionable on the back, neck, and head of the person. The support board is conformable to the back, neck, and back of the person. The support board includes a main section having a generally rectangular configuration. The main section is positionable on the back of the person. The main section has an upper edge, a lower edge, and opposed side edges. The main section has a pair of hand receiving apertures therethrough inwardly of the opposed side edges. The support board includes an upper section extending upwardly from the main section. The upper section has an upper edge, a lower edge, and opposed side edges. The upper section is positionable under the neck and head of the person. The lower edge of the upper section is contiguous with the upper edge of the main section. A plurality of straps are coupled with the support board for securing the support board to the person. Each of the straps are adjustable. The plurality of straps include a pair of cross straps extending between the opposed side edges of the main section of the support board whereby the cross straps extend across a torso of the person. The plurality of straps include a pair of diagonal straps having upper ends secured to the opposed side edges of the upper section of the support board and lower ends secured to the opposed side edges of the main section. The diagonal straps are extendable over shoulders of the person. The plurality of straps include a forehead strap extending between the opposed side edges of the upper section downwardly of the upper edge thereof for extending over a forehead of the person. The plurality of straps include a chin strap extending between the opposed side edges of the upper section downwardly of the forehead strap for extending over a chin of the person.

There has thus been outlined, rather broadly, the more MS important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved extricating device for persons with spinal injuries which has all the advantages of the prior art immobilization devices and none of the disadvantages.

It is another object of the present invention to provide a new and improved extricating device for persons with spinal injuries which may be easily and efficiently manufactured and marketed.

It is a further object of the present invention to provide a new and improved extricating device for persons with spinal injuries which is of durable and reliable construction.

An even further object of the present invention is to provide a new and improved extricating device for persons with spinal injuries which is susceptible of a low cost of manufacture with regard to both materials and labor, and which accordingly is then susceptible of low prices of sale to the consuming public, thereby making such an extricating device for persons with spinal injuries economically available to the buying public.

Even still another object of the present invention is to provide a new and improved extricating device for persons with spinal injuries for allowing a person having a spinal injury to be moved from a seated position to a horizontal position and onto an awaiting long board.

Lastly, it is an object of the present invention to provide a new and improved extricating device for persons with spinal injuries including a support board positionable on the back, neck, and head of the person. The support board is conformable to the back, neck, and back of the person. The support board includes a main section and an upper section extending upwardly from the main section. The upper section is AS positionable under the neck and head of the person. A plurality of straps are coupled with the support board for securing the support board to the person. Each of the straps are adjustable.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various figures.

DESCRIPTION OF THE PREFERRED EMBODIMENT

Figure 1:
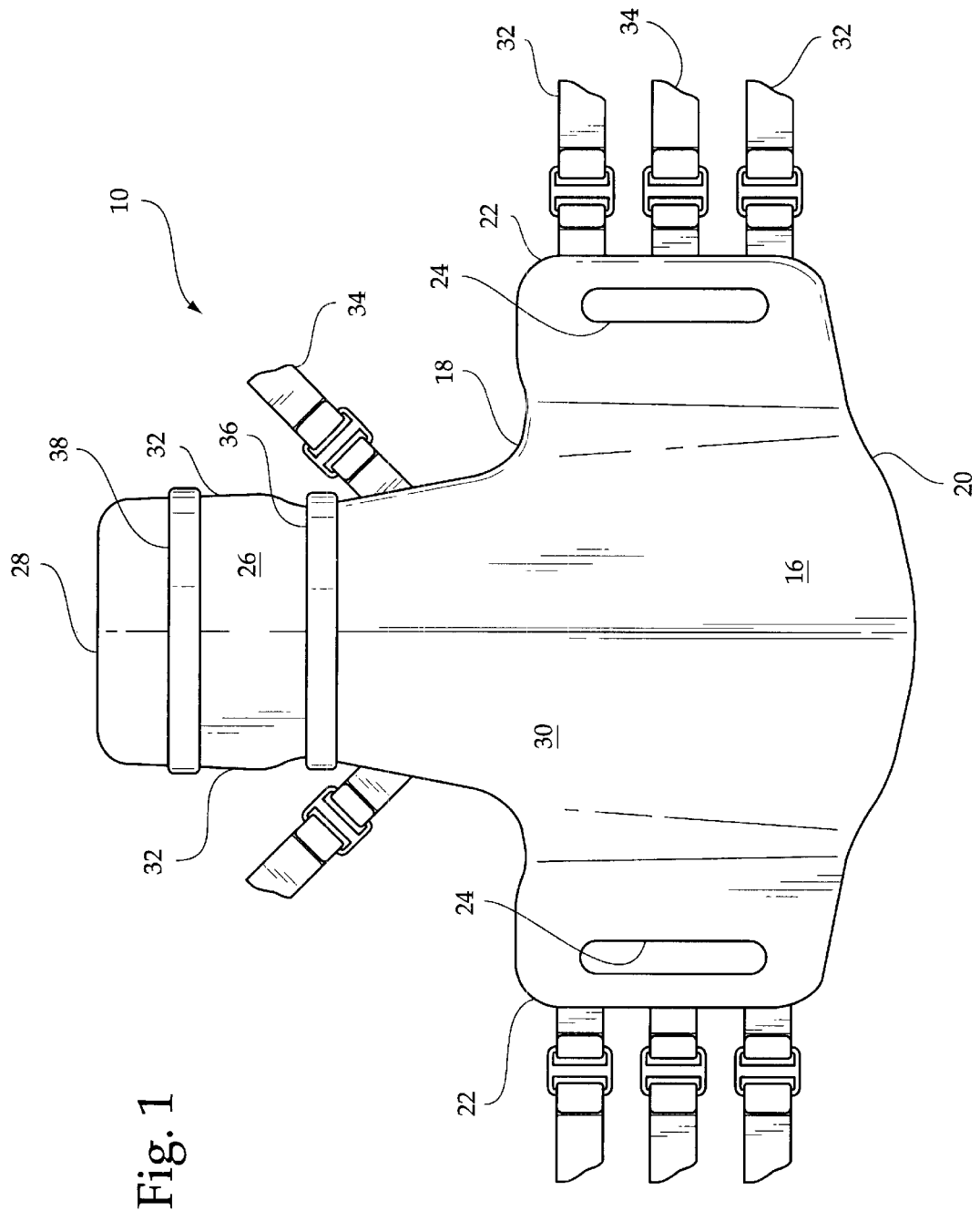
FIG. 1 is a perspective view of the preferred embodiment of the extricating device for persons with spinal injuries constructed in accordance with the principles of the present invention.
Figure 2:
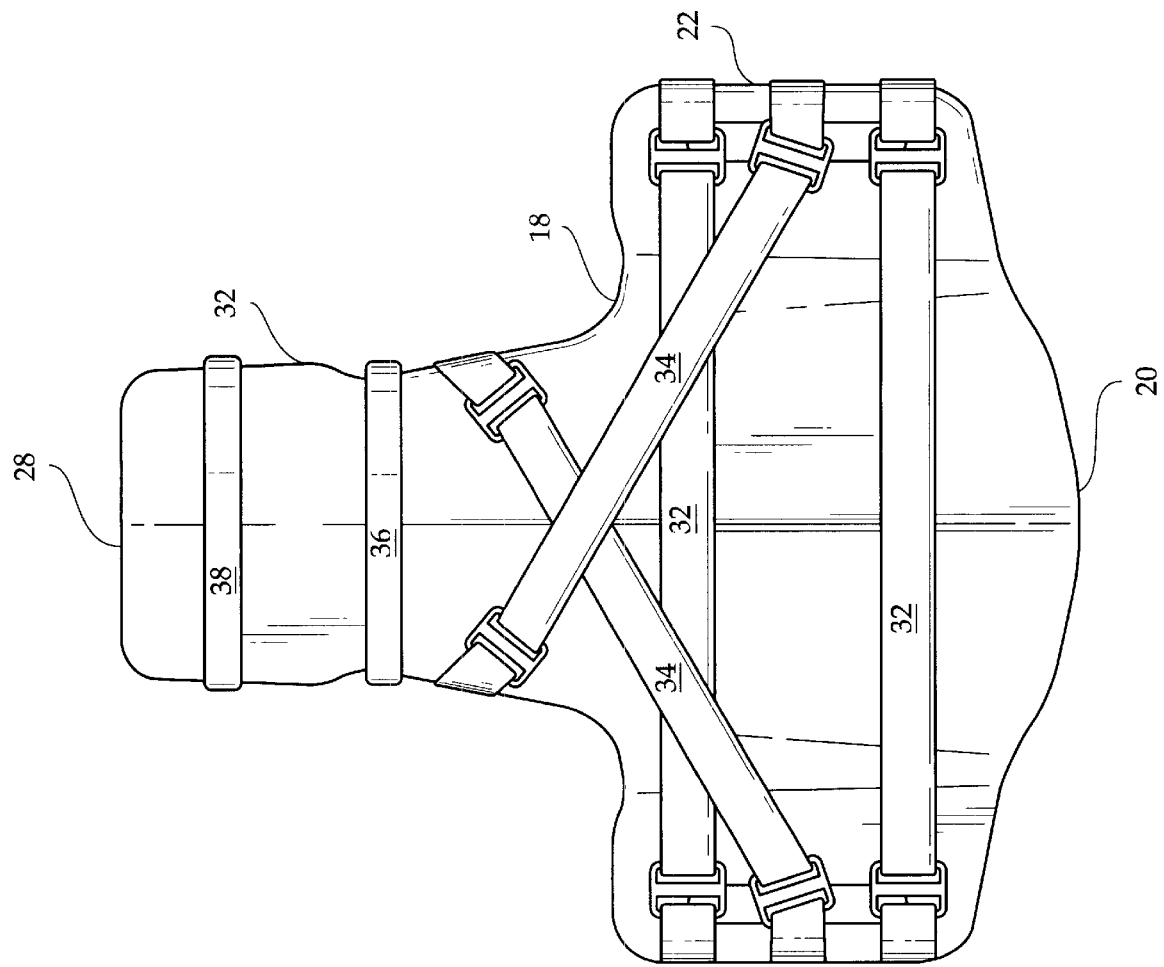
FIG. 2 is a rear view of the present invention.
Figure 3:
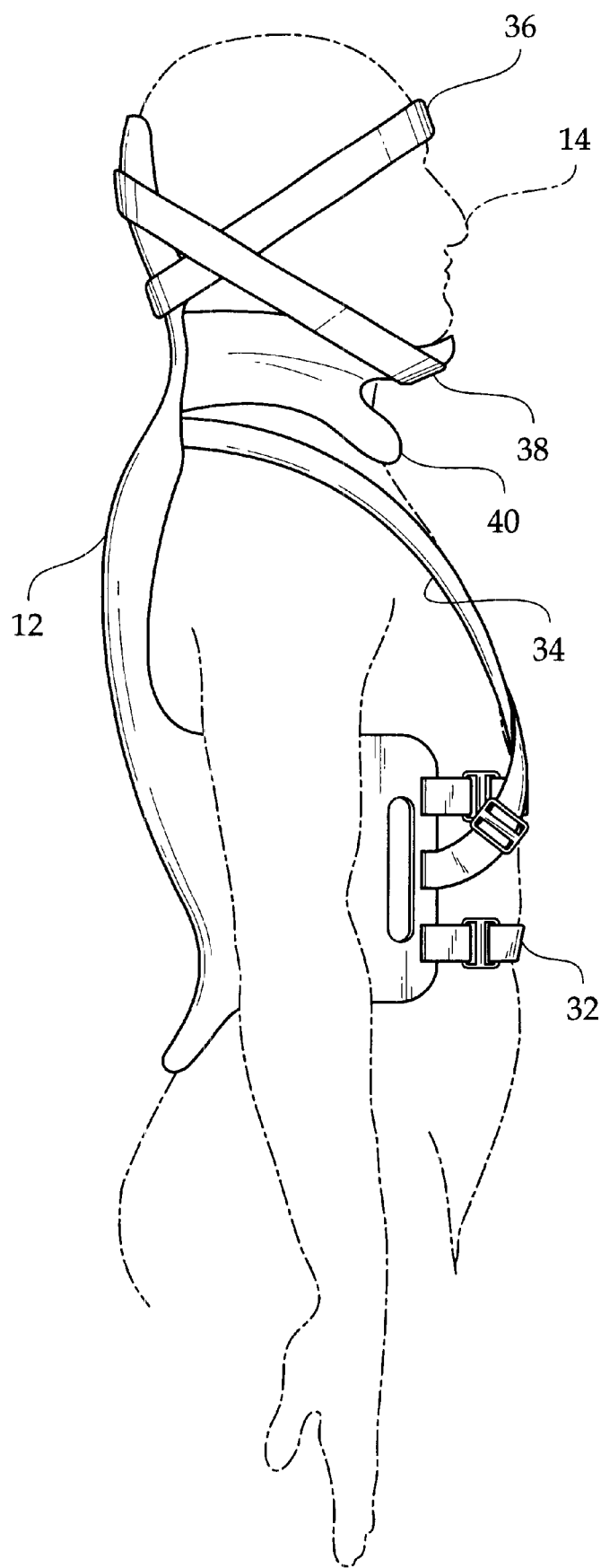
FIG. 3 is a side view of the present invention illustrated in use.

With reference now to the drawings, and in particular, to FIGS. 1 through 3 thereof, the preferred embodiment of the new and improved extricating device for persons with spinal injuries embodying the principles and concepts of the present invention and generally designated by the reference number 10 will be described.

Specifically, it will be noted in the various figures that the device relates to an extricating device for persons with spinal injuries for allowing a person having a spinal injury to be moved from a seated position to a horizontal position and onto an awaiting long board. In its broadest context, the device consists of a support board and a plurality of straps. Such components are individually configured and correlated with respect to each other so as to attain the desired objective.

The support board 12 is positionable on the back, neck, and head of the person 14. The support board 12 is conformable to the back, neck, and back of the person 14. The support board 12 is generally rigid, but can bend to conform to the shape of the person 14. Note FIG. 3. The support board 12 includes a main section 16 having a generally rectangular configuration. The main section 16 is positionable on the back of the person 14. The main section 16 has an upper edge 18, a lower edge 20, and opposed side edges 22. It should be noted that the upper edge 18 and the lower edge 22 are slightly curved to conform to the shape of the back of the person 14. The main section 16 has a pair of hand receiving apertures 24 therethrough inwardly of the opposed side edges 22. The hand receiving apertures 24 allow the support board 12 to be handled while in place on the person 14 without directly contacting the person 14 to reduce the risk of further injury. The support board 12 includes an upper section 26 extending upwardly from the main section 16. The upper section 26 has an upper edge 28, a lower edge 30, and opposed side edges 32. The upper section 26 is positionable under the neck and head of the person 14. The lower edge 30 of the upper section 26 is contiguous with the upper edge 28 of the main section 16. The support board 12 can be constructed in one size or could be constructed in different sizes to accommodate all accident victims.

The plurality of straps are coupled with the support board 12 for securing the support board 12 to the person 14. Each of the straps are adjustable. This allows the support board 12 to be properly tightened around the person because each person has different dimensions. The plurality of straps include a pair of cross straps 32 extending between the opposed side edges 22 of the main section 16 of the support board 12 whereby the cross straps 32 extend across a torso of the person 14. The plurality of straps include a pair of diagonal straps 34 having upper ends secured to the opposed side edges 32 of the upper section 26 of the support board 12 and lower ends secured to the opposed side edges 22 of the main section 16. The diagonal straps 34 are extendable over shoulders of the person 14. The plurality of straps include a forehead strap 36 extending between the opposed side edges 32 of the upper section 26 downwardly of the upper edge 28 thereof for extending over a forehead of the person 14. The plurality of straps include a chin strap 38 extending between the opposed side edges 32 of the of the upper section 26 upwardly of the forehead strap 36 for extending over a chin of the person 14. The forehead strap 36 and the chin strap 38 will criss-cross when secured to the head of the person to properly secure the support board 12 in place on the head to prevent movement.

The present invention is a device that helps move accident victims without further damaging their spine in emergency situations. The device 10 helps get the person from a seated position to a horizontal position and onto a long board. The device 10 makes the job easier and safer for patients in an automobile accident. The device 10 can be used by firemen, paramedics, police, 1st response, ambulance personnel, and the military. Additionally, the present invention would be used in conjunction with a neck brace 40.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An extricating device for persons with spinal injuries for allowing a person having a spinal injury to be moved from a seated position to a horizontal position and onto an awaiting long board comprising, in combination:

a support board positionable on the back, neck, and head of the person, the support board being conformable to the back, neck, and back of the person, the support board including a main section having a generally rectangular configuration, the main section being positionable on the back of the person, the main section having an upper edge, a lower edge, and opposed side edges, the main section having a pair of hand receiving apertures therethrough inwardly of the opposed side edges, the support board including an upper section extending upwardly from the main section, the upper section having an upper edge, a lower edge, and opposed side edges, the upper section being positionable under the neck and head of the person, the lower edge of the upper section being contiguous with the upper edge of the main section; and a plurality of straps coupled with the support board for securing the support board to the person, each of the straps being adjustable, the plurality of straps including a pair of cross straps extending between the opposed side edges of the main section of the support board whereby the cross straps extend across a torso of the person, the plurality of straps including a pair of diagonal straps having upper ends secured to the opposed side edges of the upper section of the support board and lower ends secured to the opposed side edges of the main section, the diagonal straps being extendable over shoulders of the person, the plurality of straps including a forehead strap extending between the opposed side edges of the upper section downwardly of the upper edge thereof for extending over a forehead of the person, the plurality of straps including a chin strap extending between the opposed side edges of the of the upper section downwardly of the forehead strap for extending over a chin of the person.

2. An extricating device for persons with spinal injuries for allowing a person having a spinal injury to be moved from a seated position to a horizontal position and onto an awaiting long board comprising, in combination:

a support board positionable on the back, neck, and head of the person, the support board being conformable to the back, neck, and back of the person, the support board including a main section having a generally rectangular configuration, the main section being positionable on the back of the person, the support board including an upper section extending upwardly from the main section, the upper section being positionable under the neck and head of the person; and a plurality of straps coupled with the support board for securing the support board to the person, each of the straps being adjustable the straps including a pair of diagonal straps having upper ends secured to opposed side edges of the upper section of the support board and lower ends secured to opposed side edges of the main section, the diagonal straps being extendable over shoulders of the person.

\* \* \* \* \*